(12) United States Patent
Schweiger et al.

(10) Patent No.: US 6,620,747 B2
(45) Date of Patent: Sep. 16, 2003

(54) LOW TEMPERATURE-SINTERING APATITE GLASS CERAMIC

(75) Inventors: Marcel Schweiger, Chur (CH); Volker Rheinberger, Vaduz (LI); Wolfram Höland, Schaan (LI)

(73) Assignee: Ivoclar Vivadent AG, Liechtenstein (LI)

( * ) Notice: Subject to any disclaimer, the term of this patent is extended or adjusted under 35 U.S.C. 154(b) by 136 days.

(21) Appl. No.: 09/887,417

(22) Filed: Jun. 22, 2001

(65) Prior Publication Data

US 2002/0022563 A1 Feb. 21, 2002

Related U.S. Application Data

(60) Provisional application No. 60/245,870, filed on Nov. 3, 2000.

(30) Foreign Application Priority Data

Jun. 28, 2000 (DE) .......................... 100 31 430

(51) Int. Cl.$^7$ .......................... C03C 10/02; A61C 13/083
(52) U.S. Cl. .......................... 501/10; 501/3; 428/428; 428/701; 433/212.1; 433/228.1
(58) Field of Search ................. 501/3, 2, 10; 433/212.1, 433/228.1; 106/35; 428/428, 701

(56) References Cited

U.S. PATENT DOCUMENTS

| | | | |
|---|---|---|---|
| 5,641,347 A | | 6/1997 | Grabowski et al. |
| 6,121,175 A | | 9/2000 | Drescher et al. |
| 6,200,137 B1 | | 3/2001 | Höland et al. |
| 6,280,863 B1 | * | 8/2001 | Frank et al. ............. 428/701 |
| 6,306,784 B1 | * | 10/2001 | Drescher et al. ............. 501/59 |

FOREIGN PATENT DOCUMENTS

| | | |
|---|---|---|
| CA | 2239865 | 6/1998 |
| EP | 0 885 855 A2 | 5/1998 |
| EP | 0 885 856 A2 | 5/1998 |
| GB | 2 320 023 A | 6/1998 |

* cited by examiner

*Primary Examiner*—Karl Group
(74) *Attorney, Agent, or Firm*—Nixon Peabody LLP

(57) ABSTRACT

A low-temperature-sintering apatite glass ceramic is described which is characterized by a high chemical stability, a low coefficient of expansion as well as high translucency and which is particularly suitable on its own or together with glasses or other glass ceramics as coating or veneering material for ceramic dental restorations.

25 Claims, No Drawings

LOW TEMPERATURE-SINTERING APATITE GLASS CERAMIC

This application claims the benefit of U.S. Provisional Patent Application No. 60/245,870, filed Nov. 3, 2000.

The invention relates to a low-temperature-sintering apatite glass ceramic which is suitable in particular for use in restorative dentistry and above all for coating or veneering dental restorations, such as ligaments, veneers, bridges or crowns.

Glass ceramics for use in dentistry are known from the state of the art.

EP-A-0 690 030 discloses leucite-containing phosphosilicate glass ceramics which can be used in dental technology. However, they have very high linear thermal coefficients of expansion because of their leucite content, so that they are not suitable for coating materials with low coefficients of expansion, such as e.g. lithium disilicate glass ceramics.

Furthermore, alkali-zinc-silicate glass ceramics are disclosed in EP-A-0 695 726 which can however contain only 8.0 wt.-% ZnO at most, for which reason their chemical resistance is still not satisfactory in every case. These glass ceramics have moreover the disadvantage that they contain no apatite but leucite as crystal phase. Due to the high coefficient of expansion of leucite, the glass ceramics are therefore as a rule likewise not suitable as coatings for lithium disilicate glass ceramics.

Apatite glass ceramics have also already been used in restorative dentistry.

EP-A-885 855 and EP-A-885 856 describe apatite glass ceramics with optical properties which come close to those of natural teeth. They show a good resistance under the conditions of the oral environment and are derived from the chemical system $SiO_2$—$Al_2O_3$—$P_2O_5$—$K_2O$—$Na_2O$—$CaO$—F. Additional components are possible but only in relatively small amounts. So the ZnO content is limited to 5.0 wt.-% at most and that of $K_2O$ to 8.5 wt.-% at most. Due to these restrictions, a combination of good chemical resistance and low sintering temperature can still not be achieved in every case with these materials.

A further disadvantage of these glass ceramics is that, as a rule, they cannot be sintered onto a ceramic or glass ceramic dental framework, such as a lithium disilicate glass ceramic at low temperatures of less than 800C. However, it is precisely when preparing thin-walled dental restorations, such as thin-walled veneers, also sometimes referred to as ligaments, that stresses and fractures of the dental restoration occur, because of the necessary high temperatures. Thus, in particular dental veneers with a core made from lithium disilicate glass ceramic and apatite glass ceramic sintered onto it cannot be prepared in a satisfactory way according to the state of the art.

Furthermore, the satisfactory processing of the known glass ceramics by sintering is possible only in a narrow temperature range. When there are larger deviations from the actual sintering temperature, these glass ceramics show an unsatisfactory dimensional stability in the case of too high a temperature and an unacceptably high porosity in the case of too low a temperature after sintering. The satisfactory workability only in a narrow temperature range is very disadvantageous, as the furnaces used for the preparation of dental restorations are small, and it is thus generally difficult to constantly maintain a desired temperature in them over a certain period of time. Particularly in furnaces which operate at low temperatures, such as lower than 850° C., considerable fluctuations in temperature occur during a sintering process.

The object of the invention is accordingly to prepare an apatite glass ceramic which is similar in its optical properties and in particular in its high translucency to natural tooth material and has an excellent chemical resistance and a low thermal coefficient of expansion. Furthermore, the apatite glass ceramic is to have a low sintering temperature so that it is above all suitable as coating or veneering material for preparing stable thin-walled dental restorations, such as dental veneers. Finally, the glass ceramic is to be able to be processed to produce the desired restorations in a wide temperature range.

This object is surprisingly achieved by the low-temperature-sintering apatite glass ceramic according to claims 1 to 9.

The subject-matter of the invention are also the process for preparing the apatite glass ceramic according to claim 10, the dental material according to claims 11 to 14, the use according to claims 15 to 18 as well as the shaped dental products according to claims 19 to 22.

The apatite glass ceramic according to the invention is characterized in that it comprises the following components:

| Component | wt.- % |
|---|---|
| $SiO_2$ | 56.0 to 65.0 |
| $Li_2O$ | 1.8 to 5.3 |
| $K_2O$ | 9.0 to 17.5 |
| ZnO | 9.0 to 16.0 |
| CaO | 3.5 to 10.5 |
| $P_2O_5$ | 2.0 to 6.0 |
| F | 0.5 to 1.0 | and the main crystalline phase is formed by apatite crystals.

The glass ceramic according to the invention can additionally comprise at least one of the following components:

| Component | wt. - % |
|---|---|
| $Na_2O$ | 0 to 5.0 |
| MgO | 0 to 3.5 |
| SrO | 0 to 3.5 |
| $Al_2O_3$ | 0 to 6.0 |
| $B_2O_3$ | 0 to 2.0 |
| $La_2O_3$ | 0 to 3.0 |
| $ZrO_2$ | 0 to 7.5 |
| $TiO_2$ | 0 to 7.5 |
| $CeO_2$ | 0 to 2.0 |
| $SnO_2$ | 0 to 5.0 |
| $Tb_4O_7$ | 0 to 0.5. |

If these additional components are present, they are used in particular in amounts of at least 0.1 wt.-%.

For the individual components of the apatite glass ceramic according to the invention, there are preferred quantity ranges. These can be selected, unless otherwise stated, independently of each other and are as follows:

| Component | wt. - % |
|---|---|
| $SiO_2$ | 56.0 to 64.0 |
| $Li_2O$ | 2.0 to 5.0 |
| $K_2O$ | 9.5 to 16.0 |
| ZnO | 9.0 to 15.0 |
| CaO | 4.0 to 10.0 |
| $P_2O_5$ | 2.0 to 5.0 |
| F | 0.5 to 0.9 |

-continued

| Component | wt. - % |
|---|---|
| $Na_2O$ | 0 to 4.0 |
| MgO | 0 to 3.0 |
| SrO | 0 to 3.0 |
| $Al_2O_3$ | 0 to 5.0 |
| $B_2O_3$ | 0 to 1.8 |
| $La_2O_3$ | 0 to 2.5 |
| $ZrO_2$ | 0 to 6.0 |
| $TiO_2$ | 0 to 6.0 |
| $CeO_2$ | 0 to 1.8 |
| $SnO_2$ | 0 to 4.0 |
| $Tb_4O_7$ | 0 to 0.4. |

Particularly preferred quantity ranges for the individual components of the apatite glass ceramic according to the invention are as follows and these can be selected independently of each other:

| Component | wt. - % |
|---|---|
| $SiO_2$ | 56.0 to 63.0 |
| $Li_2O$ | 2.5 to 5.0 |
| $K_2O$ | 10.0 to 15.0 |
| ZnO | 9.0 to 14.0 |
| CaO | 4.0 to 9.0 |
| $P_2O_5$ | 2.5 to 5.0 |
| F | 0.5 to 0.8 |
| $Na_2O$ | 0 to 3.0 |
| MgO | 0 to 2.5 |
| SrO | 0 to 2.5 |
| $Al_2O_3$ | 0 to 4.0 |
| $B_2O_3$ | 0 to 1.5 |
| $La_2O_3$ | 0 to 2.0 |
| $ZrO_2$ | 0 to 5.0 |
| $TiO_2$ | 0 to 5.0 |
| $CeO_2$ | 0 to 1.5 |
| $SnO_2$ | 0 to 3.0 |
| $Tb_4O_7$ | 0 to 0.3 |

All the above quantity amounts in wt.-% relate to the glass ceramic.

The glass ceramic according to the invention can furthermore contain e.g. usual color components for matching to the colour of the natural tooth material of a patient.

It was ascertained by scanning electron microscope and x-ray diffraction studies that apatite, such as hydroxy apatite, and/or fluoroapatite, forms the main crystal phase in the glass ceramic. The apatite crystals have grown hexagonally for preference, and in particular in a needle-shaped manner. At their greatest extension, the apatite crystals are preferably than 10 μm, in particular smaller than 7 μm and particularly preferably smaller than 5 μm.

The optical properties of the glass ceramic are controlled by the separated apatite crystals, which are similar in appearance to the carbonate-apatite crystals of natural tooth material. Thus it is possible that a glass ceramic is produced with an appearance which corresponds to that of dentine or enamel of a tooth. Simultaneously, an optical depth effect is achieved in the glass ceramic, such as is not possible with other types of crystals.

Leucite crystals are not radiographically detectable in the glass ceramic according to the invention, but secondary crystal phases such as e.g. sodium-calcium orthophosphate of the $NaCaPO_4$ type may be present.

A further particular advantage of the glass ceramic according to the invention is that, due to its particular composition, it has not only a high chemical resistance and translucency, but also a particularly desired low sintering temperature.

The glass ceramic according to the invention normally has a very advantageous sintering temperature of less than 800° C. during sintering onto a ceramic or glass-ceramic substrate, such as a lithium disilicate glass ceramic. Those glass ceramics according to the invention are particularly preferred which have a sintering temperature of 780° C. and below and thus can be processed at this temperature. These low sintering temperatures are presumably attributable to the special composition of the glass ceramic according to the invention.

It is of particular advantage that the glass ceramic according to the invention can also be worked by sintering even where there are large deviations from the actual sintering temperature, i.e. the temperature at which the dimensional stability as well as the porosity of the glass ceramic are particularly satisfactory. Thus the glass ceramic can even be processed in a sintering temperature range of ±200° C., or more, such as e.g. ±400° C., above or below the actual sintering temperature without cracks or faults occurring in the dental restoration. When working in this temperature range, the sintered glass ceramic has a very low porosity and a very good dimensional stability. An indication of the excellent dimensional stability is that even the very thin-walled incisor edge, which has been formed by applying a mixture of glass ceramic powder and admixing liquid to a framework as well as its shaping, retains its form after the sintering process and thus lasts. Thus, the glass ceramic according to the invention can also be sintered in furnaces which do not permit a precise control of the firing temperature, which is particularly advantageous. On the other hand, conventional glass ceramics permit only deviations of ±100° C. from the sintering temperature. With larger deviations, satisfactory restorations cannot be prepared with them.

Furthermore, the apatite-glass ceramic normally has a low thermal coefficient of expansion of 9.3 to 10.8 $\times 10^{-6} K^{-1}$, measured in the temperature range of 100° C. to 400° C.

For the preparation of the apatite glass ceramic according to the invention a) a starting glass which contains the above stated components is melted at temperatures of 1200° C. to 1650° C., b) the obtained glass melt is poured into water accompanied by formation of a glass granulate, c) the glass granulate is optionally reduced to a glass powder with an average particle size of 1 to 450 μm, relative to the number of particles, and d) the glass granulate or the glass powder is subjected to a thermal treatment at more than 500° C. and up to 900° C. for a period of 30 minutes to 6 hours.

In stage (a), a starting glass is firstly melted, by intimately mixing suitable starting materials, such as for example carbonates, oxides and fluorides, with each other and heating to the stated temperatures.

Then in stage (b), the obtained glass melt is quenched by being poured into water and thereby transformed into a glass granulate. This procedure is customarily also called fritting.

The glass granulate is optionally then reduced in stage (c) and is ground to the desired particle size in particular with customary mills. The obtained glass powder preferably has an average particle size of 1 to 450 μm, relative to the number of particles.

In stage (d), the glass granulate or optionally the glass powder is subjected to a thermal treatment at a temperature in the range of more than 500° C. and up to 900° C. for a period of 30 minutes to 6 hours, preferably 30 minutes to 3 hours. Contrary to the conventional apatite-glass ceramics, it is possible to carry out the temperature treatment and thus the production of the apatite crystals at temperatures of less than 900° C., which is without question an advantage.

A volume crystallisation takes place during the thermal treatment. This leads to a homogenous distribution of the apatite crystals inside the entire glass ceramic, in contrast to the leucite crystallisation, which can take place only on the inner surfaces of a glass powder.

It was ascertained by scanning electron microscope and x-ray diffraction studies that apatite, preferably fluoroapatite, forms the main crystal phase. The size of the obtained crystals can be controlled by the selected temperature and the period of thermal treatment. In addition to the apatite crystals, further crystals phases can be formed depending on the chemical composition of the starting glass used.

Alongside the different crystal phases, microheterogenous separation areas, i.e. different glass phases, may also be present. These areas can be recognised in the scanning electron microscope as small microheterogenous glass drop phases with a size of approx. 20 to 400 nm. Together with the crystals, the glass drop phases occurring influence the optical properties of the glass ceramics according to the invention, such as e.g. opalescence and translucency.

Surprisingly, the optical properties of the apatite glass ceramic according to the invention can be adjusted from glassy-transparent to cloudy white. This is absolutely necessary for the use as dental material or component thereof in order to be able to reproducibly prepare all the different variations of natural teeth. The fine apatite crystals in the structure of the glass ceramic according to the invention have a very great similarity to natural teeth in terms of optics and structure.

The apatite glass ceramic according to the invention is therefore preferably used as dental material either on its own or together with further components. To this end, it is normally used in the form of a powder with an average particle size of less than 90 μm. Glasses and other glass ceramics, but also color components, in particular colored pigments, oxides of the 3d elements or metal colloids, as well as fluorescence materials, in particular ytterbium silicate doped with d- and f-elements, can also be considered as further components. It is preferred that the dental material contains 10 to 90 wt.-% of the apatite glass ceramic.

When using the apatite glass ceramic as a component of dental material, dental materials can by obtained by suitable selection of their composition as well as the type of the further components in which important properties, such as e.g. working temperature, optical properties, thermal coefficient of expansion and chemical resistance, are matched exactly to the respective demands. This is often not possible with pure glass ceramics.

Dental material is particularly advantageous which contains as further component at least a glass and preferably a potassium-zinc- silicate glass.

A potassium-zinc-silicate glass is preferred which comprises the following components:

| Component | wt. - % |
|---|---|
| $SiO_2$ | 60.0 to 72.0 |
| $Li_2O$ | 1.0 to 5.0 |
| $K_2O$ | 10.0 to 23.0 |
| ZnO | 8.5 to 20.0 |

This glass can additionally comprise at least one of the following components:

| Component | wt. - % |
|---|---|
| $Na_2O$ | 0 to 4.0 |
| MgO | 0 to 4.0 |
| CaO | 0 to 3.6 |
| SrO | 0 to 3.0 |
| $Al_2O_3$ | 0 to 8.0 |
| $B_2O_3$ | 0 to 3.3 |
| $La_2O_3$ | 0 to 3.0 |
| $ZrO_2$ | 0 to 6.0 |
| $TiO_2$ | 0 to 2.5 |
| $CeO_2$ | 0 to 2.0 |
| $SnO_2$ | 0 to 5.0 |
| $P_2O_5$ | 0 to 1.0 |
| $Tb_4O_7$ | 0 to 1.8 |
| F | 0 to 1.1. |

If these additional components are present, they are used in particular in amounts of at least 0.1 wt.-%.

The above amounts in wt.-% relate to the potassium-zinc-silicate glass.

The potassium-zinc-silicate glass can be prepared in the customary way, e.g. by melting a corresponding amount of suitable oxides, carbonates and fluorides in a platinum/rhodium crucible at a temperature of 1550° C. to 1600° C. for a homogenization time of 1 to 1.5 hours. If desired, the glass melt can then be quenched in water, and the formed granulate dried and ground to a desired particle size.

The obtained potassium-zinc-silicate glass is characterized by a high translucency, high chemical resistance as well as a low coefficient of expansion. It is moreover excellently matched in its chemical composition to the apatite glass ceramic according to the invention, so that disadvantageous material transport reactions between both materials and an ensuing build-up of stress are avoided in particular in case of thin layered composites.

The dental material according to the invention normally has a linear thermal coefficient of expansion of 9.0 to $10.9 \times 10^{-6}$ $K^{-1}$, measured in the range of 100° C. to 400° C. The respectively desired coefficient can be set by suitable choice of the type of apatite glass ceramic and any further components, as well as their amounts. Favourable dental materials contain 10 to 90 wt.-% apatite glass ceramic and 90 to 10 wt.-% further components, relative to the dental material.

The dental material according to the invention is suitable for coating substrates and in particular for coating or veneering dental restorations. The coating takes place in particular by applying the dental material to the selected substrate and subsequent sintering at less than 800° C. and in particular 760° C. or less.

Preferably a powder of the apatite glass ceramic according to the invention is firstly mixed with a powder of the optionally present further components and worked to a paste by adding aqueous admixing solutions. This paste is then applied to the substrate and after desired shaping sintering takes place in order to obtain a firmly adhering coating or veneer.

The dental material according to the invention can be used as coating or veneering material for substrates such as dental suprastructures e.g. based on ceramic or glass ceramic materials. Due to its low coefficient of expansion, it is preferably used in substrate materials with a thermal coefficient of expansion of 7.0 to 12.0, in particular 8.0 to $11.0 \times 10^{-6} K^{-1}$. It is preferably used for coating or veneering $ZrO_2$ ceramics, $Al_2O_3$ ceramics, $ZrO_2/Al_2O_3$ ceramics, ceramic or glass ceramic composite materials and titanium.

It is particularly advantageously used however to veneer substrates based on lithium disilicate glass ceramic in order to in this way prepare aesthetically very attractive all-ceramic dental products which have a very high strength as well as an excellent chemical resistance.

Lithium disilicate glass ceramics which contain the following components and which can be obtained e.g. by melting of suitable starting glasses, fritting and thermal treatment at 400° C. to 1100° C., have proved particularly suitable:

| Component | wt. - % |
|---|---|
| $SiO_2$ | 57.0 to 80.0 |
| $Al_2O_3$ | 0 to 5.0 |
| $La_2O_3$ | 0.1 to 6.0 |
| MgO | 0 to 5.0 |
| ZnO | 0 to 8.0 |
| $Li_2O$ | 11.0 to 19.0 |
| $P_2O_5$ | 0 to 11.0 | where

| | | | |
|---|---|---|---|
| (a) | $Al_2O_3 + La_2O_3$ | account for | 0.1 to 7.0 wt. - % |
| and | | | |
| (b) | MgO + ZnO | account for | 0.1 to 9.0 wt. - %. |

The amounts in wt.-% relate to the lithium disilicate glass ceramic.

The apatite glass ceramic according to the invention and the dental material according to the invention can be worked into shaped dental products in the usual way together with the optionally present additives. Dental restorations such as e.g. an inlay, an onlay, a bridge, a stump reconstruction, a veneer, a facette, a filling or a connector can be considered in particular as dental products shaped according to the invention which contain apatite glass ceramic or the dental material. Ligaments, veneers, bridges, crowns and part-crowns are particularly preferred dental restorations.

The dental products preferably have a core based on ceramic or glass ceramic material, in particular lithium disilicate glass ceramic, to which the glass ceramic according to the invention or the dental material according to the invention is applied. Preferred lithium disilicate glass ceramics have already been described above.

In contrast to conventional glass ceramics, the glass ceramic according to the invention is even better suited in its chemical composition to glasses, such as potassium-zinc-silicate glasses, and lithium disilicate glass ceramics which are preferably used as further components of a coating material or as a substrate. The consequence of this is that precisely with thin layered composites, such as e.g. thin-walled veneers, with lithium disilicate glass ceramic as substrate to which a mixture of apatite glass ceramic according to the invention and potassium-zinc-silicate glass has been applied, there are no signs of separation of the coating or a fracture of the finished product. The low sintering temperature of the glass ceramic according to the invention is also responsible for this advantageous behaviour.

In addition, the glass ceramic according to the invention shows an excellent chemical resistance, which is imperative for its use as dental material, around which acid liquids wash permanently in the oral cavity. It is surprising that the glass ceramic has both a good chemical resistance and a low sintering temperature. This favourable combination of properties is possibly attributable to the fact that the glass ceramic simultaneously contains several types of alkali metal ions.

The invention is explained in more detail below using examples.

EXAMPLES

Examples 1 to 31

In total, 31 different glass ceramics according to the invention were prepared. They had the chemical compositions listed in Table I.

TABLE I

Composition of apatite glass ceramics according to the invention (figures in wt.-%)

| No. | $SiO_2$ | $Li_2O$ | $K_2O$ | ZnO | $P_2O_5$ | CaO | F | $Na_2O$ | MgO | SrO | $B_2O_3$ | $Al_2O_3$ | $La_2O_3$ | $TiO_2$ | $ZrO_2$ | $SnO_2$ | $CeO_2$ | $Tb_4O_7$ |
|---|---|---|---|---|---|---|---|---|---|---|---|---|---|---|---|---|---|---|
| 1 | 61.5 | 4.6 | 11.7 | 10.7 | 3.6 | 6.1 | 0.6 | 1.2 | | | | | | | | | | |
| 2 | 61.4 | 4.3 | 13.6 | 10.6 | 3.5 | 6.1 | 0.5 | | | | | | | | | | | |
| 3 | 59.4 | 4.1 | 16.5 | 10.0 | 3.5 | 6.0 | 0.5 | | | | | | | | | | | |
| 4 | 63.5 | 4.3 | 13.6 | 8.5 | 3.5 | 6.1 | 0.5 | | | | | | | | | | | |
| 5 | 59.5 | 4.2 | 13.2 | 10.3 | 3.4 | 5.9 | 0.4 | | | | | | 3.1 | | | | | |
| 6 | 63.3 | 5.0 | 12.9 | 11.0 | 2.7 | 4.6 | 0.5 | | | | | | | | | | | |
| 7 | 56.5 | 4.1 | 12.9 | 10.0 | 3.3 | 5.8 | 0.4 | | | | | | 3.2 | | 3.8 | | | |
| 8 | 58.0 | 4.0 | 12.7 | 9.9 | 3.3 | 5.7 | 0.4 | | | | | | 6.0 | | | | | |
| 9 | 56.9 | 4.0 | 12.5 | 9.8 | 3.3 | 5.6 | 0.4 | | | | | | | | 7.5 | | | |
| 10 | 56.9 | 4.0 | 12.5 | 9.8 | 3.3 | 5.6 | 0.4 | | | | | | | 7.5 | | | | |
| 11 | 58.9 | 3.5 | 11.6 | 16.0 | 3.5 | 6.0 | 0.5 | | | | | | | | | | | |
| 12 | 57.9 | 4.6 | 11.8 | 10.1 | 5.4 | 9.2 | 1.0 | | | | | | | | | | | |
| 13 | 59.2 | 4.6 | 11.8 | 8.9 | 5.4 | 9.2 | 0.9 | | | | | | | | | | | |
| 14 | 60.5 | 4.3 | 13.5 | 10.6 | 3.9 | 6.7 | 0.5 | | | | | | | | | | | |
| 15 | 57.6 | 4.2 | 13.2 | 10.3 | 3.4 | 5.9 | 0.4 | | | | | | | | 5.0 | | | |
| 16 | 59.7 | 4.3 | 13.5 | 10.5 | 3.5 | 6.0 | 0.5 | | | | | 2.0 | | | | | | |
| 17 | 58.5 | 4.2 | 13.4 | 10.4 | 3.5 | 6.0 | 0.5 | | | 3.5 | | | | | | | | |
| 18 | 59.5 | 4.2 | 13.4 | 10.4 | 3.5 | 6.0 | 0.5 | | | | | | | | | | 2.0 | 0.5 |
| 19 | 58.5 | 4.2 | 13.4 | 10.4 | 3.5 | 6.0 | 0.5 | | 3.5 | | | | | | | | | |
| 20 | 60.5 | 4.3 | 13.6 | 10.6 | 3.5 | 7.0 | 0.5 | | | | | | | | | | | |
| 21 | 65.0 | 5.0 | 12.8 | 11.2 | 2.0 | 3.5 | 0.5 | | | | | | | | | | | |
| 22 | 62.6 | 5.0 | 12.9 | 11.0 | 2.7 | 5.3 | 0.5 | | | | | | | | | | | |
| 23 | 60.6 | 5.3 | 12.2 | 10.7 | 3.6 | 7.1 | 0.5 | | | | | | | | | | | |

TABLE I-continued

Composition of apatite glass ceramics according to the invention (figures in wt.-%)

| No. | SiO$_2$ | Li$_2$O | K$_2$O | ZnO | P$_2$O$_5$ | CaO | F | Na$_2$O | MgO | SrO | B$_2$O$_3$ | Al$_2$O$_3$ | La$_2$O$_3$ | TiO$_2$ | ZrO$_2$ | SnO$_2$ | CeO$_2$ | Tb$_4$O$_7$ |
|---|---|---|---|---|---|---|---|---|---|---|---|---|---|---|---|---|---|---|
| 24 | 56.0 | 4.6 | 11.9 | 10.1 | 6.0 | 10.5 | 0.9 | | | | | | | | | | | |
| 25 | 61.8 | 3.4 | 9.1 | 10.6 | 3.5 | 6.1 | 0.5 | 5.0 | | | | | | | | | | |
| 26 | 60.7 | 1.8 | 17.5 | 12.2 | 2.6 | 4.6 | 0.6 | | | | | | | | | | | |
| 27 | 58.5 | 4.3 | 12.2 | 10.6 | 3.5 | 6.1 | 0.5 | 0.9 | 1.3 | | | | | 0.3 | 1.0 | | 0.8 | |
| 28 | 57.8 | 4.3 | 13.5 | 10.5 | 3.5 | 6.0 | 0.5 | | 1.3 | | | | | | 2.0 | | 0.6 | |
| 29 | 59.6 | 4.2 | 13.4 | 10.4 | 3.5 | 6.0 | 0.5 | | | | | | | | 1.9 | | 0.5 | |
| 30 | 58.4 | 4.3 | 13.4 | 10.5 | 3.6 | 4.4 | 0.5 | 1.0 | 1.3 | | | | | | 2.0 | | 0.6 | |
| 31 | 57.6 | 4.3 | 13.4 | 10.5 | 3.9 | 4.9 | 0.5 | 1.0 | 1.3 | | | | | | 2.0 | | 0.6 | |

For their preparation, a corresponding amount of suitable oxides, carbonates and fluorides was melted to produce a starting glass each time in a platinum/rhodium crucible at a temperature of 1500° C. to 1550° C. for a homogenization time of 1 h. The glass melt was quenched in water, and the granulate formed from the starting glass was dried and ground to an average particle size of less than 90 μm, relative to a number of particles.

Subsequently, the granulate or the obtained powder of the starting glass was subjected to a single or multi-stage thermal treatment for 30 minutes to 6 hours at more than 500° C. and up to 900° C., whereupon the corresponding glass ceramic formed.

For some of the glass ceramics, selected properties are listed in Table II which have been measured in test pieces made from the respective glass ceramic. Furthermore, details concerning the specifically selected thermal treatment of the starting glass are found in Table II under "Thermal treatment".

Measurement of the Coefficient of Expansion α

To measure the linear thermal coefficient of expansion α, a rod-shaped green body was prepared from powder of the respective glass ceramic, and was sintered in a vacuum firing furnace at a heating-up rate of 60° C./min and with a holding time of 1 minute at the respectively stated firing temperature for the preparation of the test pieces. Subsequently a glaze firing was carried out without vacuum at a final temperature which was 20° C. higher and with a holding time of 1 minute. The linear thermal coefficient of expansion was measured on the obtained test piece in the temperature range of 100 to 400° C.

Measurement of the Acid Resistance

The acid resistance is a measure of the chemical resistance especially of glass ceramics used in the dental field, as these are permanently exposed to the action of acid substances in the oral cavity.

The acid resistance was measured according to ISO-specification 6872:1995. To this end, small test plates with a diameter of 12 mm and a thickness of 1 mm were firstly prepared by sintering together glass ceramic powder with an average particle size of 90 μm. The powder was maintained at the sintering temperature for 1 minute. Then the small test plates were treated for 16 hours with 4 vol.-% aqueous acetic acid at 80° C., and finally the loss of weight which had occurred, relative to the surface of the small plates, was determined as a measure of the acid resistance.

TABLE II

Properties of apatite glass ceramics according to the invention

| No. | Thermal treatment | α-value × 10$^{-6}$ K$^{-1}$ [100–400° C.] | Tg [° C.] | optical | firing temp. on crown [° C.] | acid resistance [μg/cm$^2$] | firing temp. for the preparation of test pieces [° C.] |
|---|---|---|---|---|---|---|---|
| 1 | 800° C./1 hr | 10.41 | 469 | cloudy | 670 | 30 | 750 |
| 2 | 520° C./4 hr + 800°/1 hr | 9.39 | 476 | milky cloudy | 730 | 27 | 810 |
| 4 | 550° C./2 hr + 800°/1 hr | 9.95 | — | milky cloudy | 730 | 4 | 810 |
| 6 | 520° C./4 hr + 800°/1 hr | 9.46 | 471 | milky cloudy | 740 | 8 | 820 |
| 8 | 800° C./1 hr | 10.45 | 526 | opaque | 780 | 16 | 860 |
| 18 | 800° C./1 hr | 10.24 | 492 | translucent | 710 | 29 | 790 |
| 21 | 800° C./1 hr | 9.72 | 485 | translucent opal | 700 | 42 | 780 |
| 28 | 520° C./4 hr + 800°/1 hr | — | — | translucent opal | 780 | 39 | 850 |
| 29 | 520° C./4 hr + 800°/1 hr | — | — | translucent opal | 780 | 26 | 850 |

The "firing temperature on crown" denotes the temperature at which the glass ceramic was able to be sintered onto a crown framework made from glass ceramic material.

The examples illustrate how glass ceramics with different properties can be obtained by changing the chemical composition.

The examples illustrate how glass ceramics with different properties can be obtained by changing the chemical composition.

Example 32

This example describes the use of a mixture of the apatite glass ceramic according to the invention according to example 29 together with a potassium-zinc-silicate glass as a coating material for ceramic suprastructures and thus its usability for the preparation of all-ceramic dental products.

The potassium-zinc-silicate glass used had the composition (in wt.-%):

SiO2 65.2; Li$_2$O 4.2; K$_2$O 14.8; ZnO 12.8; MgO 0.6; ZrO$_2$ 1.9; CeO$_2$ 0.5.

For the preparation of this potassium-zinc-silicate glass, a corresponding amount of starting materials was melted in a platinum/rhodium crucible at a temperature of 1550° C. to 1600° C. for a homogenization time of 1 to 1.5 hours. The glass melt was quenched in water, and the granulate formed from the starting glass was dried and ground to an average particle size of less than 90 μm.

To obtain a coating material in which sintering temperature and coefficients of expansion are suitably set, 50 wt.-% of the apatite glass ceramic according to the invention were mixed with 50 wt.-% of the glass in the form of powders with an average particle size of less than 90 μm.

This mixture was sintered to produce a rod-shaped green body in a vacuum furnace at a heating-up rate of 60° C./min and with a holding time of 1 min at 8400° C. For the test piece thus obtained, a thermal coefficient of expansion of $9.96 \times 10^{-6} K^{-1}$ was determined, measured in the temperature range of 100° C. to 400° C.

Thus this mixture was able to be used for sintering onto a very translucent lithium disilicate glass ceramic with a thermal coefficient of expansion of $10.6 \times 10^{31}$ $^6K^{-1}$. It is shown that the sintering-on of the mixture was already possible at a temperature of only 730° C. Overall, all-ceramic dental products such as crowns or bridges, were thus able to be prepared which are characterized by an excellent bonding of the individual layers, an aesthetically pleasing appearance and good chemical stability.

Example 33

Preparation of a Thin-walled Veneer

A thin-walled veneer for a middle upper incisor with a layer thickness of max. 0.5 mm was prepared from a lithium disilicate glass ceramic by compression in the viscous state. After the hot pressing, the layer thickness was reduced to max 0.25 mm by mechanical reworking with a diamond tool. The surface of the veneer was then cleaned in an aqueous solution of 0.5 vol.-% HF and 3 vol. -% H$_2$SO$_4$ for 10 minutes in an ultrasound bath and then sand-blasted with Al$_2$O$_3$ at a jet pressure of 1.5 bar. A dental material was then sintered on, this being a mixture of the glass ceramic No. 2 according to the invention and a potassium-zinc-silicate glass. The potassium-zinc-silicate glass used had the composition (in wt.-%):

SiO$_2$: 64.0; Li$_2$O: 4.0; K$_2$O: 12.6; ZnO: 12.4; Al$_2$O$_3$: 3.2; ZrO$_2$: 3.8.

For the preparation of this potassium-zinc-silicate glass, a corresponding amount of starting materials was melted in a platinum/rhodium crucible at a temperature of 1550° C. to 1600° C. for a homogenization time of 1 to 1.5 hours. The glass melt was quenched in water, and the granulate formed was dried and ground to an average particle size of less than 90 μm.

To obtain a coating material in which sintering temperature and coefficient of expansion are suitably set, 50 wt.-% of the apatite glass ceramic according to the invention were mixed with 50 wt.-% of the potassium-zinc-silicate glass in the form of powders with an average particle size of less than 90 μm. The thermal coefficient of expansion of this dental material was $9.4 \times 10^{-6} K^{-1}$. The sintering temperature was 750° C. and was maintained for 1 minute during the coating of the veneer. A total of 5 firings were carried out with material application at 750° C. until the veneer was completed. The final glaze firing was carried out at 740° C. without vacuum in order to achieve a superficial inherent shine. The veneer representing a dental restoration showed a very homogenous layer bonding. No cracks or faults formed, which is not usual with such thin-walled products. The veneer furthermore showed a very good translucency, which is an extremely important property in this form of dental restoration.

Example 34

Preparation of a 3-Membered Front Tooth Bridge

A front tooth bridge framework with an intermediate member was prepared from a lithium disilicate glass ceramic by compression in the viscous state. The smallest wall thickness was approx. 0.5 mm. After the hot pressing, the framework was cleaned with an aqueous solution of 0.5 vol.-% HF and 3 vol.-% H$_2$SO$_4$ in an ultrasound bath for 10 minutes and subsequently sand-blasted with Al$_2$O$_3$ at a jet pressure of 1.5 bar. Then a dental material was sintered on which consisted of the apatite glass ceramic No. 28 according to the invention and a potassium-zinc-silicate glass. The potassium-zinc-silicate glass used had the composition (in wt.-%):

SiO$_2$: 65.2; Li$_2$O: 4.2; K$_2$O: 14.8; ZnO: 12.8; MgO: 0.6; ZrO$_2$: 1.9; CeO$_2$: 0.5.

For the preparation of this potassium-zinc-silicate glass, a corresponding amount of starting materials was melted in a platinum/rhodium crucible at a temperature of 1550° C. to 1600° C. for a homogenization time of 1 to 1.5 hours. The glass melt was quenched in water, and the granulate formed from the glass was dried and ground to an average particle size of less than 90 μm.

To obtain a coating material in which sintering temperature and coefficient of expansion are suitably set, 50 wt.-% of the apatite glass ceramic according to the invention were mixed with 50 wt.-% of the potassium-zinc-silicate glass in the form of powders with an average particle size of less than 90 gm. The thermal coefficient of expansion of this dental material was $10.0 \times 10^{-6} K^{-1}$. The sintering temperature was 730° C. and was maintained for 1 minute in each case during the coating of the framework. A total of 5 firings were carried out with material application at 730° C. until the front tooth bridge was completed. The final glaze firing was carried out at 720° C. without vacuum in order to achieve a superficial inherent shine. The obtained three-membered front tooth bridge showed a homogenous bond between lithium disilicate framework and sintering material. No cracks or faults formed in the bridge, due to the matched thermal coefficient of expansion, the low sintering temperature and the chemical compatibility between the individual components.

What is claimed is:

1. Low-temperature-sintering apatite glass ceramic, which comprises the following components:

| Component | wt.- % |
|---|---|
| $SiO_2$ | 56.0 to 65.0 |
| $Li_2O$ | 1.8 to 5.3 |
| $K_2O$ | 9.0 to 17.5 |
| ZnO | 9.0 to 16.0 |
| CaO | 3.5 to 10.5 |
| $P_2O_5$ | 2.0 to 6.0 |
| F | 0.5 to 1.0. |

2. Apatite glass ceramic according to claim 1, which further comprises at least one of the following components:

| Component | wt. - % |
|---|---|
| $Na_2O$ | 0 to 5.0 |
| MgO | 0 to 3.5 |
| SrO | 0 to 3.5 |
| $Al_2O_3$ | 0 to 6.0 |
| $B_2O_3$ | 0 to 2.0 |
| $La_2O_3$ | 0 to 3.0 |
| $ZrO_2$ | 0 to 7.5 |
| $TiO_2$ | 0 to 7.5 |
| $CeO_2$ | 0 to 2.0 |
| $SnO_2$ | 0 to 5.0 |
| $Tb_4O_7$ | 0 to 0.5. | and has a main crystalline phase formed of apatite crystals.

3. Apatite glass ceramic according to claim 1, wherein the amounts of the following individual components are selected independently of each other:

| Component | wt. - % |
|---|---|
| $SiO_2$ | 56.0 to 64.0 |
| $Li_2O$ | 2.0 to 5.0 |
| $K_2O$ | 9.5 to 16.0 |
| ZnO | 9.0 to 15.0 |
| CaO | 4.0 to 10.0 |
| $P_2O_5$ | 2.0 to 5.0 |
| F | 0.5 to 0.9 |
| $Na_2O$ | 0 to 4.0 |
| MgO | 0 to 3.0 |
| SrO | 0 to 3.0 |
| $Al_2O_3$ | 0 to 5.0 |
| $B_2O_3$ | 0 to 1.8 |
| $La_2O_3$ | 0 to 2.5 |
| $ZrO_2$ | 0 to 6.0 |
| $TiO_2$ | 0 to 6.0 |
| $CeO_2$ | 0 to 1.8 |
| $SnO_2$ | 0 to 4.0 |
| $Tb_4O_7$ | 0 to 0.4. |

4. Apatite glass ceramic according to claim 1, wherein the amounts of the following individual components are selected independently of each other:

| Component | wt. - % |
|---|---|
| $SiO_2$ | 56.0 to 63.0 |
| $Li_2O$ | 2.5 to 5.0 |
| $K_2O$ | 10.0 to 15.0 |
| ZnO | 9.0 to 14.0 |
| CaO | 4.0 to 9.0 |
| $P_2O_5$ | 2.5 to 5.0 |
| F | 0.5 to 0.8 |
| $Na_2O$ | 0 to 3.0 |
| MgO | 0 to 2.5 |
| SrO | 0 to 2.5 |
| $Al_2O_3$ | 0 to 4.0 |
| $B_2O_3$ | 0 to 1.5 |
| $La_2O_3$ | 0 to 2.0 |
| $ZrO_2$ | 0 to 5.0 |
| $TiO_2$ | 0 to 5.0 |
| $CeO_2$ | 0 to 1.5 |
| $SnO_2$ | 0 to 3.0 |
| $Tb_4O_7$ | 0 to 0.3. |

5. Apatite glass ceramic according to claim 1, which has a sintering temperature of less than 800° C.

6. Apatite glass ceramic according to claim 1, which has a sintering temperature from 670 to 780° C.

7. Apatite glass ceramic according to claim 1, wherein the apatite crystals are needle-shaped.

8. Apatite glass ceramic according to claim 1, wherein the apatite crystals are smaller than 10 μm at their greatest extension.

9. Apatite glass ceramic according to claim 1, which has a linear thermal coefficient of expansion of 9.3 to $10.8 \times 10^{-6} K^{-1}$, measured in the temperature range of 100° C. to 400° C.

10. Process for preparing the apatite glass ceramic according to claim 1, comprising the following steps:
   a) a starting glass which comprises the components according to claim 1 is melted at temperatures of 1200° C. to 1650° C.,
   b) the obtained glass melt is poured into water to form a glass granulate,
   c) the glass granulate is optionally reduced to produce a glass powder with an average particle size of 1 to 450μm, and
   d) the glass granulate or the glass powder is subjected to a thermal treatment at more than 500° C. and up to 900° C. for a period of 30 minutes to 6 hours.

11. Dental material, which comprises the apatite glass ceramic according to claim 1.

12. Dental material according to claim 11, which additionally comprises a potassium-zinc-silicate glass.

13. Dental material according to claim 12, wherein the potassium-zinc-silicate glass comprises the following components:

| Component | wt. - % |
|---|---|
| $SiO_2$ | 60.0 to 72.0 |
| $Li_2O$ | 1.0 to 5.0 |
| $K_2O$ | 10.0 to 23.0 |
| ZnO | 8.5 to 20.0. |

14. Dental material according to claim 11, which has a sintering temperature of less than 800° C.

15. A method for coating comprising coating a substrate with the dental material according to claim 11.

16. The method according to claim 15, wherein the substrate is based on ceramic or glass ceramic material.

17. The method according to claim 25, wherein the lithium disilicate glass ceramic comprises the following components:

| Component | wt. - % |
|---|---|
| $SiO_2$ | 57.0 to 80.0 |
| $Al_2O_3$ | 0 to 5.0 |
| $La_2O_3$ | 0.1 to 6.0 |
| MgO | 0 to 5.0 |
| ZnO | 0 to 8.0 |
| $Li_2O$ | 11.0 to 19.0 |
| $P_2O_5$ | 0. to 11.0 | where a) $Al_2O_3+La_2O_3$ account for 0.1 to 7.0 wt.-% and b) MgO+ZnO account for 0.1 to 9.0 wt.-%.

18. The method according to claim 15, wherein the dental material is applied to the substrate and sintered at temperatures of less than 800° C.

19. Shaped dental product, which comprises the apatite glass ceramic according to claim 1.

20. Shaped dental product according to claim 19, which is a dental restoration.

21. Shaped dental product according to claim 19, which has a core- based on ceramic or glass ceramic material, and a coating applied to it comprising the apatite glass ceramic.

22. Shaped dental product according to claim 21, wherein the glass ceramic material is a lithium disilicate glass ceramic.

23. The method according to claim 15, wherein the substrate comprises a dental restoration.

24. Shaped dental product, which comprises the dental material according to claim 11.

25. The method according to claim 16, wherein the substrate is a lithium disilicate glass ceramic.

* * * * *